United States Patent [19]

Wilson et al.

[11] Patent Number: 4,847,246

[45] Date of Patent: Jul. 11, 1989

[54] ANTIVIRAL COMPOSITIONS DERIVED FROM FIREFLIES AND THEIR METHODS OF USE

[76] Inventors: George R. Wilson, 2011 Cureton Dr.; Kenneth L. Rinehart, 1306 S. Carle Ave., both of Urbana, Ill. 61801

[21] Appl. No.: 96,337

[22] Filed: Sep. 11, 1987

[51] Int. Cl.[4] .................... A61K 31/585; C07J 17/00
[52] U.S. Cl. .................................. 514/175; 540/105
[58] Field of Search ................... 540/105; 514/175

[56] References Cited

· PUBLICATIONS

Merck Index, 10th Edition (1983), #1438, Bufalin.
Journal of the American Chemical Society, vol. 101, No. 11, May 23, 1979, pp. 3055–3060; Meinwald et al.

*Primary Examiner*—Douglas W. Robinson
*Assistant Examiner*—Joseph A. Lipovsky
*Attorney, Agent, or Firm*—Morgan & Finnegan

[57] ABSTRACT

This invention relates to antiviral organic steroid compositions and derivatives thereof; a process of producing the antiviral compositions; and a method for inhibiting viruses utilizing the compositions. More particularly, the compositions are derived from fireflies of the genus, Photinus.

16 Claims, No Drawings

ANTIVIRAL COMPOSITIONS DERIVED FROM FIREFLIES AND THEIR METHODS OF USE

FIELD OF THE INVENTION

This invention relates to organic compounds which have useful antiviral activity. More particularly, this invention relates to methods of making and using organic lucibufagin antiviral compositions derived from fireflies, *Photinus pyralis*.

BACKGROUND OF THE INVENTION

Viral diseases afflict man, plants, insects, and animals. The prevention and control of viral diseases have important health and economic implications.

Viral diseases contribute to afflictions in humans including common colds, herpes, and cancer, and the importance of their control is obvious. It is important to control viral diseases in animals for economic reasons and because animals, including insects can become virus reservoirs or carriers which facilitate the spreading of viral diseases to humans. Further, viral plant diseases have been known to disrupt the growth of commercial plant crops, including fruit trees, tobacco, and various vegetables.

The prevention and control of viral diseases are thus of prime importance to man, and considerable research has been devoted to antiviral measures. Certain methods and chemical compositions have been developed which aid in inhibiting, controlling or destroying viruses, but additional methods and antiviral chemical compositions are needed.

A potential source for antiviral compositions is plant and animal life and of particular interest herein is the firefly.

Previous work reported by Meinwald et al. and Goetz, et al. has indicated that Photinus can be a source of lucibufagin compounds. Such work has been reported in the following references. Meinwald et al., *J. Am. Chem. Soc.*, 101: 11, (1979) Pp. 3055–3060, (discloses esters of 12-oxo-2,5,11-trihydroxybufalin derived from the firefly Photinus, see compounds 5, 6, 11 and 12); Goetz et al. *Experientia*, 37, (1981), Pp. 679–680 (discloses esters of 12-oxo-2,5,11-trihydroxybufalin derived from the firefly *Photinus pyralis*, see compounds 1–6); Eisner et al, *Proc. Natl. Acad. Sci. USA*, Vol. 75, No. 2, (1978), pp. 905–908 (discloses lucibufagins derived from firefly *Photinus ignitus* and *P. marginellus*); and Goetz et al., *Helv. Chim. Acta*, 62, Fasc. 5, Nr. 144 (1979), pp. 1396–1400 (discloses lucibufagins from fireflies *Photinus ignitus* and *P. marginellus*, see compounds 4 and 9). No antiviral activity was reported for any of the above-identified compounds. The entire disclosures of all of the above-noted literature references are hereby incorporated herein by reference.

It has been found by the present inventors that certain lucibufagin compounds, derived from fireflies, have antiviral activity.

SUMMARY OF THE INVENTION

It is therefore an object of the invention to provide compounds which are useful as active agents in antiviral compositions.

Additional objects and advantages of the invention will become apparent in the description which follows and in part will be obvious from this description of the present invention. The advantages of the invention are realized and obtained by means of the compositions, processes, methods, and the combinations particularly pointed out in the appended claims.

To achieve the objects in accordance with the purposes of the invention, as embodied and fully described herein, the invention comprises antiviral compounds of the general formula (I):

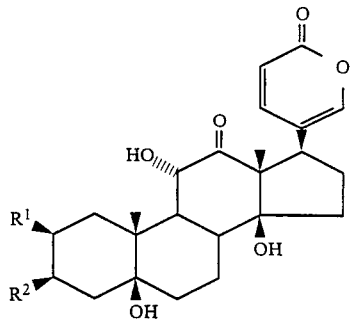

wherein $R^1$ and $R^2$ are the same or different and are a hydroxyl or lower acyloxy group of from 1 to 6 carbon atoms.

In preferred embodiments of the invention, the compound is substantially pure. In further preferred embodiments the lower aclyoxy groups have from 2 to 4 carbon atoms.

As embodied and fully described herein, the invention comprises an antiviral composition comprising, as active agent, an effective antiviral amount of one or more compounds according to formula I. In more preferred embodiments of the invention, the active ingredient comprises compounds of formula I wherein $R^1$ is hydroxy or acetoxy and $R^2$ is hydroxy or acetoxy. In further preferred embodiments the active ingredient comprises one or more compounds of the formulae (II–VI):

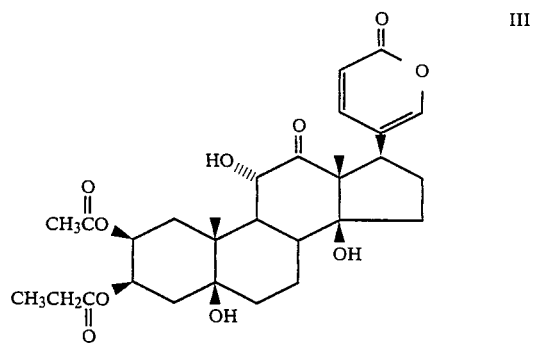

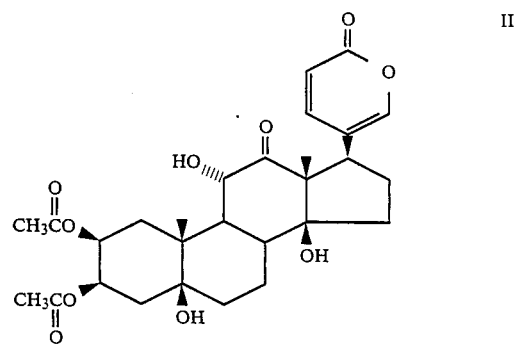

-continued

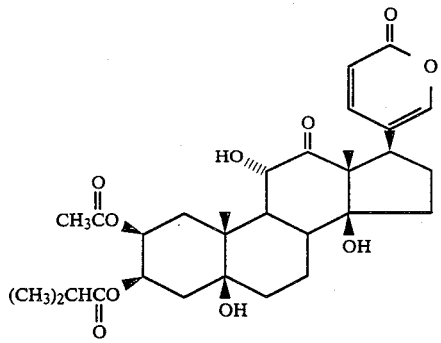
IV

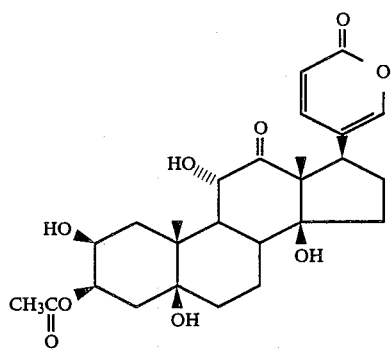
V

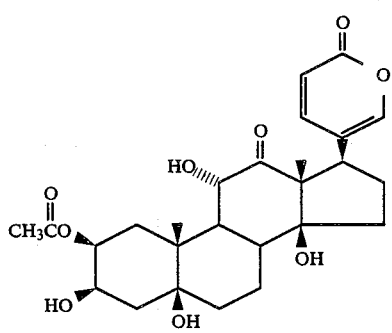
VI

As embodied and fully described herein, the invention comprises a method for inhibiting viruses comprising contacting a virus with an effective antiviral amount of one or more compounds according to formulae I–VI.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention an antiviral composition is provided comprising as active agent an effective antiviral amount of one or more of the compounds described above and identified by formula I:

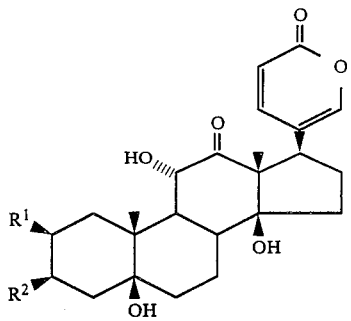
I wherein $R^1$ and $R^2$ are the same or different and are a hydroxyl or lower acyloxy group of from 1 to 6 carbon atoms and a non-toxic pharmaceutically acceptable carrier or diluent.

In preferred embodiments of the invention, the compounds is substantially pure. In further preferred embodiments of the lower acyloxy groups have from 2 to 4 carbon atoms.

In more preferred embodiments of the invention, the invention comprises compounds of formulae (II–VI):

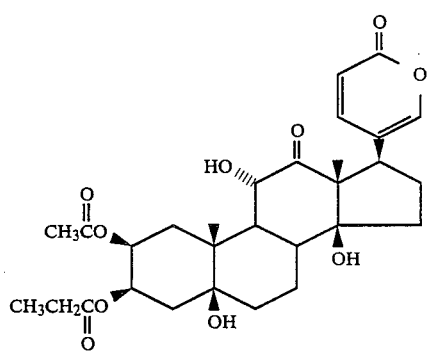
III

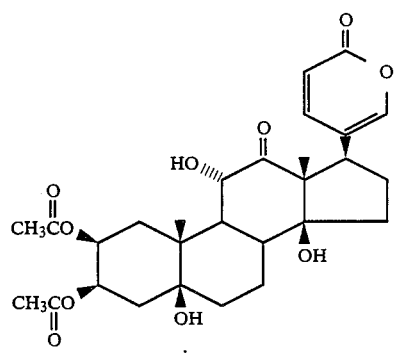
II

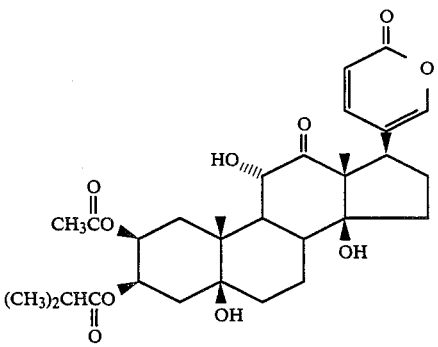
IV

-continued

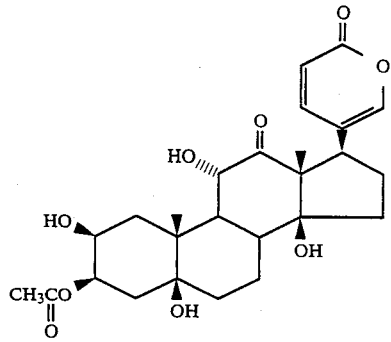

V

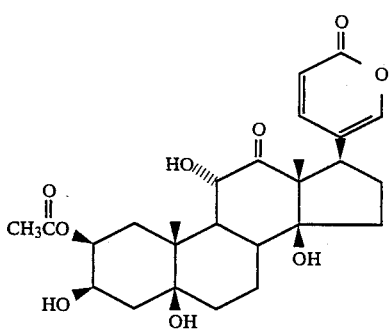

VI and a non-toxic pharmaceutically acceptable carrier or diluent.

In accordance with the present invention, viruses are inhibited or killed by a method comprising contacting a virus with an effective antiviral amount of one or more compounds according to formulae I–VI.

While effective amounts may vary, as conditions in which the antiviral compositions are used vary, a minimal dosage required for activity is generally between 3 and 30 nanograms against 25 to 80 plaque-forming units of virus.

The minimal antiviral effective amount of the antiviral compositions of the invention as stated above is generally from 3 to 30 nanograms against 25 to 80 plaque-forming units of virus cells. The compounds of formulae I–VI are active in inhibiting or killing a diverse range of viruses including, but not limited to, RNA viruses, e.g., vesicular stomatitis (herein "VSV"), arenaviruses, corona-viruses, rhinoviruses, reoviruses, polioviruses, influenza viruses and the DNA viruses, e.g., herpes simplex-I (herein "HSV-I"), other herpes viruses, adenoviruses, coxsackie viruses, and papovaviruses. The effectiveness of the compositions of the invention for inhibiting viruses indicates their usefulness for controlling viral infections in host animals and plants which are caused by a virus which is thus inhibited or destroyed.

As embodied and fully described herein, the invention also comprises a new process to produce the compounds of formulae I–VI. A detailed description and explanation of a preferred embodiment of the process of the invention to produce the compounds according to formulae I–VI is as follows.

A quantity of *Photinus pyralis* fireflies is collected and contacted with a first organic solvent and homogenized to form an extract. The organic solvent is removed by evaporation leaving a mixture of solids and yellow oil. Alternatively, the solution in the first organic solvent is partitioned by liquid/liquid fractionation and the solvent is removed from the actual fraction by evaporation to yield a solid or a mixture of solids and oil. The mixture is then partially dissolved in a second organic solvent and filtered. The solid residue is discarded and the filtered liquid solution is subjected to chromatography to obtain and isolate the compounds according to formulae I–VI. The chromatography product is separated into fractions which contain the desired compositions. Specific compositions according to the invention are thus isolated by various chromatographic techniques from the fractions obtained.

Ethyl acetate is the presently preferred choice for the first and second organic solvents, however, other suitable solvents may be substituted for ethyl acetate. Suitable solvents which may be substituted for ethyl acetate include, but are not limited to, the following organic solvents: benzene, hexane, toluene, chloroform, methylene chloride, butyl acetate, butanol, acetone, acetonitrile, ethanol, methanol and mixtures thereof. Different ratios of solvent mixtures may be used for the first and second solvents in the invention as would be known to those skilled in the art.

Any suitable fractionation and isolation techniques may be utilized in accordance with the process of the invention. Suitable fractionation techniques include solvent partitioning, as for example between methanol-water mixtures and toluene, and various chromatographic techniques, such as gravity-flow, normal, or reversed-phase column chromatography using hand-packed glass columns containing absorbents, as would be known to those skilled in the art and/or high-pressure liquid chromatography with suitable commercial normal phase or reversed-phase columns as would be known to those skilled in the art (e.g., Alltech 6233 or Alltech/Applied Science 6231 columns) eluted with a suitable solvent such as, for example, ethyl acetate, benzene, hexane, chloroform, methylene chloride, butyl acetate, butanol, acetone, acetonitrile, ethanol, methanol, water and mixtures thereof.

It is therefore apparent that the compounds of the invention, the processes for producing the compounds of the invention and the methods for utilizing the compounds of the invention to inhibit viruses are effective for inhibiting or destroying viruses and therefore controlling diseases caused by or related to such viruses.

EXAMPLE 1–5

The invention will now be illustrated by examples. The examples are not intended to limit the scope of the present invention. In conjunction with the detailed and general descriptions above, the examples provide further understanding of the present invention and outline a process for producing compounds of the invention.

The following examples represent preferred embodiments of the compounds, processes and methods of the invention. The starting materials and reagents in the examples whose method of preparation are not indicated are commercially available from sources known to the art such as chemical supply houses.

Preparation of Compositions 1-5

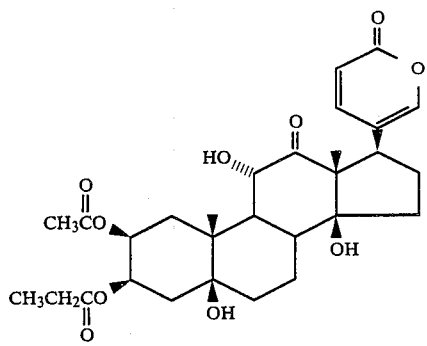

3

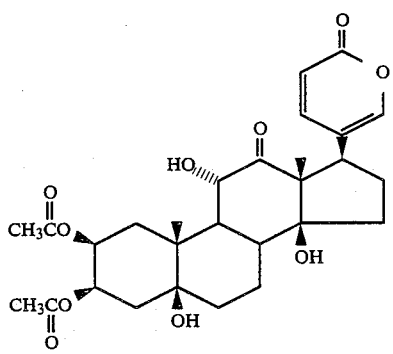

1

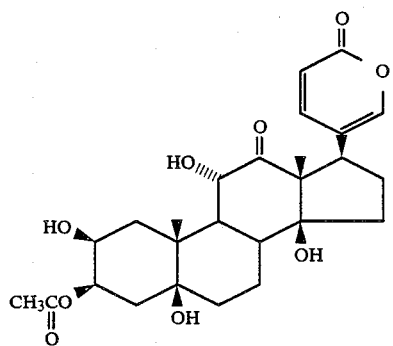

4

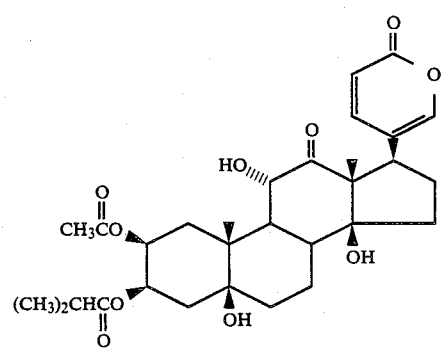

2

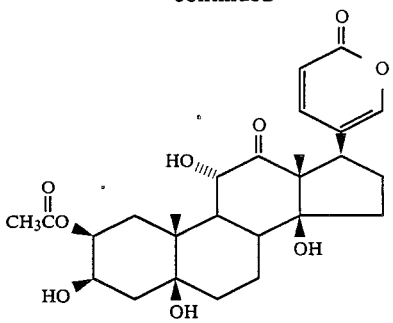

5

-continued

About 100 Photinus fireflies were collected in a single evening in Urbana, Ill., stored overnight at 20° C., weighed the following morning (4.85 gms), and divided into two approximately equal portions, each being ground 3 times for 2 minutes with 20 mL of ethyl acetate (EtOAc) at the top speed of a Virtis 45 blender equipped with a 100-mL stainless steel flask. After each grinding, the liquid extract was filtered off (Whatman #4 paper) and the solids were returned to the flask for the next grinding. The combined extracts were concentrated at 35° C. in a rotary evaporator, the residue taken up in 10 mL EtOAc and left overnight under a nitrogen stream. The following morning the mixture of solids and yellow oil (293 mg) was stored at −20° C. Days later the mixture was returned to room temperature, partly dissolved in 15 mL EtOAc, and filtered; the solids were discarded, and the liquid was passed through a commercially prepared, disposable, silica-gel packed mini-column (e.g., silica Sep Pak) using an additional 10 mL of EtOAc as a wash. The combined 25 mL yielded 169.2 mg solid by rotary evaporation at 35° C. that was dissolved in 17 mL of EtOAc and used to make 9 successive HPLC injections that were hand cut following the peak patterns on a recorder. The HPLC system included an Altex 110A pump, a Rheodyne 1725 injector, an Alltech 6233 10μ silica column (10 mm×250 mm) and a Waters variable wavelength 450 detector set at 254 or 300 nm. The lucibufagins collected from the 4.85 grams of insects were at this stage:

1. Pure 12-oxo-2,3-di-O-acetyl-2β,5β,11α-trihydroxybufalin 9.18 mg

2. Crude 12-oxo-2-O-acetyl-3-O-isobutyryl-2β,5β,11α-trihydroxybufalin 2.19 mg

3. Crude 12-oxo-2-O-acetyl-3-O-propionyl-2β,5β,11α-trihydroxybufalin 1.45 mg

4. Crude 12-oxo-3-O-acetyl-2β,5β,11α-trihydroxybufalin 3.60 mg

The crude lucibufagins listed above each contained one or more minor compounds that were removed by recutting them under slightly different HPLC conditions detailed below. During the final stages of these purifications the major peaks of the HPLC cuts from the crudes listed were consolidated with those from equivalent crudes obtained from other extractions. All crudes were stored at −20° C. prior to the final purification.

Crude 2 was purified by the same HPLC system except that 30 to 35% hexane in EtOAc was the solvent. A total of 39.31 mg of crudes yielded 32.81 mg of purified compound.

Crude 3 was purified by the same HPLC system except that 20% hexane in EtOAc was the solvent. A total of 16.34 mg of crudes yielded 9.98 mg of purified compound.

Crude 4 was repurified in an HPLC system similar to the original one except that the silica column used was a degraded one with reduced retention times (about one third of the elution volume of the derived compound versus an equivalent pristene column, e.g. Alltech 6233 column); the solvent used was EtOAc. A total of 43.49 mg of crudes yielded 27.49 mg of purified compound.

Purification of
12-oxo-2-O-acetyl-2β,5β,11α-trihydroxybufalin

The 12-oxo-2-O-acetyl-2β,5β,11α-trihydroxybufalin (5) was first noted as a major peak following the diacetyl compound in the gravity chromatography procedure used for the initial isolation of the diacetyl compound from insects which had been preserved in methanol for six months.

It was the major lucibufagin in the methanolic preserving fluid decanted from old insects after storage at ambient temperature.

An alternative method for preparing 5 is as follows: insects collected were killed by adding them to MeOH, the volume of solvent being increased as the later collections were added so that there was enough present to completely cover the dead insects. Twenty three months later, 600 mL of this fluid was poured off, filtered (Sargent-Welch grade S-32915-J paper), adjusted to a volume of 800 mL with MeOH used to wash the filter, added to a separatory funnel with 400 mL of 1N NaCL and extracted successively with 400-, 325-, 225-, and 125-mL portions of methylene chloride. The combined extracts were filtered (Whatman #4 paper), the solvent evaporated with a rotary evaporator (30° C.) and the residue left under nitrogen overnight. The resulting material was dissolved in 200 mL of 3:1 MeOH-toluene, and partitioned against 100 mL of 1N NaCl in a large separatory funnel. The lower layer did not clear, and after an hour it was centrifuged clear (2072G, 20 min). The toluene layer from the large separatory funnel and a thin layer of material from the tops of the centrifuge tubes (which was not miscible with the toluene layer) were mixed in a second separatory funnel with 100 mL of 3:1 MeOH-toluene and 50 mL of 1N NaCl. The lower milky layer from the second separatory funnel was cleared by centrifugation (2072G, 20 min) with the upper layer present in the centrifuge tubes, combined with the cleared lower layer from the large separatory funnel and extracted successively with 200 mL, 100 mL and 50 mL of $CH_2Cl_2$, to obtain a yellow solid. This solid was dissolved in 5 mL MeOH and passed through a commercially prepared, disposable, $C_{18}$-packed mini-column (e.g., $C_{18}$ Sep-Pak) with 15 mL of additional MeOH to yield, upon solvent removal, 600 mg of material that was partly dissolved in 6 mL of EtOAc which was centrifuged to clear and decanted. When dried down by evaporation under nitrogen the EtOAc solution yielded 567 mg. All of this was passed in a single injection through an Alltech/Applied Science 6231 25 cm, 10 mm i.d. 10 u $C_{18}$ column with MeOH as the solvent, a pumping rate of 6.0 mL per min and the detector set at 300 nm using the previously described HPLC system, the lucibufagins were obtained in toto as part of a single somewhat skewed peak with a retention time of about 4 minutes. The material obtained from the first part of this peak (179.3 mg) was partly dissolved in 6 mL of EtOAc, the insolubles (10 mg) removed by centrifugation and the remaining material used to make a series of 10 mg HPLC injections using the same 100% EtOAc, silica system described for the purification of the other lucibufagins. Fraction 7 cut from these injections gave 50 mg of 5. The crude fraction obtained contained a trace of at least one other material removed by further purification on an HPLC system like the previously described one, except that the solvent was 30% hexane in EtOAc, to give 30 mg of the compound sought.

(1)
12-oxo-2,3-di-O-acetyl-2β-5β-11α-trihydroxylbufalin ($C_{28}H_{36}O_2$)(lucibufagin C)

The molecular weight as determined from a high resolution FAB measurement on the molecular ion was 532.2309 for the molecule.

The FAB spectrum of 1 showed a series of peaks characteristic of the compound and its related substituents: 533 (M+H), 515(M+H−H$_2$O), 473 (M+H−CH$_3$COOH), 455 (515−CH$_3$COOH or 473−H$_2$O), 431 (473−ketene, CH$_2$CO, the ketene being derived from one of the acetyl moieties), 413 (M+H−2CH$_3$COOH, or 473−CH$_3$COOH), 395.1 (413−H$_2$O), 377 (395−H$_2$O).

| $^1$H NMR data: | | |
| PPM | Form | J(Hertz) |
| --- | --- | --- |
| 0.93 | s | — |
| 1.24 | s | — |
| 1.98 | s | — |
| 2.14 | s | — |
| 2.23 | d of d | 15.7, 3.0 |
| 2.50 | d of d | 13.5, 3.3 |
| 3.93 | d | 3.7 |
| 4.11 | d of d | 9.6, 6.9 |
| 4.40 | d of d | 10.9, 3.6 |
| 5.10 | d of t | 12.3, 3.5, 3.5 |
| 5.53 | broad d | 2.0 |
| 6.29 | d | 9.7 |
| 7.40 | d | 1.7 |
| 7.70 | d of d | 9.7, 2.5 |

The $^1$H NMR spectrum showed good agreement with the literature values (see Meinwald et al. supra) in all cases except d of d at 412.

(2)
12-oxo-2-O-Acetyl-3-O-isobutyryl-2β,5β,11α-trihydroxybufalin ($C_{30}H_{40}O_{10}$)(lucibufagin A)

The molecular weight as determined by high resolution FAB was 560.2639 for the molecule.

The FAB spectrum showed: 561 (M+H), 543 (M+H−H$_2$O), 501 (M+H−CH$_3$COOH), 483 (M+H−CH$_3$COOH−H$_2$O), 471.2 (483 H$_2$O), 455.2 (543−(CH$_2$)CHCOOH), 431 (501−(CH$_3$)$_2$CCO, the dimethylketene being derived from the isobutyryl moiety), 413 (431−H$_2$O), 395 (455−CH$_3$COOH).

| H$^1$NMR data: | | |
| PPM | Form | J(Hertz) |
| --- | --- | --- |
| 0.91 | s | — |
| 1.19 | d | 6.7 |
| 1.20 | d | 6.6 |
| 1.23 | s | — |
| 1.94 | s | — |
| 2.60 | sept | — |
| 3.92 | d | 3.6 |
| 4.09 | d of d | 9.6, 6.9 |

-continued

<u>H¹NMR data:</u>

| PPM | Form | J(Hertz) |
|---|---|---|
| 4.38 | d of d | 10.9, 3.4 |
| 5.09 | d of t | 9.4, 5.3, 5.3 |
| 5.54 | d | 2.1 |
| 6.28 | d | 9.8 |
| 7.39 | d | 1.7 |
| 7.70 | d of d | 9.8, 2.5 |

The ¹H NMR spectrum showed good agreement with the literature values.

(3) 12-oxo-2-O-acetyl-3-O-propionyl-2β,5β,11α-trihydroxybufalin ($C_{29}H_{38}O_{10}$)(lucibufagin B)

The molecular weight was determined by high resolution FAB as 546.2483 for the molecule. The FAB spectrum showed: (M+H), 529 (M+H−$H_2O$), 487 (M+H−$CH_3COOH$), 469 (487−$H_2O$), 455 (529−$CH_3CH_2COOH$), 431 (487−$CH_3CHCO$, the methylketene being derived from the propionyl group), 413 (431−$H_2O$), 395 (413−$H_2O$), 377 (395−$H_2O$).

<u>¹H NMR data:</u>

| PPM | Form | J(Hertz) |
|---|---|---|
| 0.91 | s | — |
| 1.17 | t | 7.5 |
| 1.23 | s | — |
| 1.96 | s | — |
| 3.92 | d | 3.6 |
| 4.10 | d of d | — |
| 4.38 | d of d | 10.9, 3.6 |
| 5.09 | d of t | 12.8 |
| 5.54 | d | 2.0 |
| 6.28 | d | 9.6 |
| 7.39 | d | 1.7 |
| 7.70 | d of d | 9.8, 2.5 |

The ¹H NMR spectrum showed good agreement with the literature values.

(4) 12-oxo-3-O-acetyl-2β,3β,11α-trihydroxylbufalin ($C_{26}H_{34}O_9$)(lucibufagin E)

The molecular weight was determined by high resolution FAB as 490.2223 for the molecule.

The FAB spectrum showed: 491 (M+H), 473 (491−$H_2O$), 449 (491−$CH_2CO$, the ketene being derived from the acetate moiety), 431 (491−$CH_3COOH$), 413 (473−$CH_3COOH$), 395 (413−$H_2O$), 377 (395−$H_2O$).

<u>¹H NMR data:</u>

| PPM | Form | J(Hertz) |
|---|---|---|
| 0.90 | s | — |
| 1.21 | s | — |
| 2.15 | s | — |
| 3.29 | broad s | — |
| 4.41 | d of d | 2.6, 10.9 |
| 5.37 | d | 2.5 |
| 6.29 | d | 9.9 |
| 7.39 | d | 1.6 |
| 7.69 | d of d | 9.7, 2.5 |

The ¹H NMR spectrum showed close agreement with the published NMR data for this compound.

(5) 12-oxo-3-O-acetyl-2β,3β,11α-trihydroxybufalin ($C_{26}H_{34}O_9$)(lucibufagin D)

The molecular weight was determined by high resolution FAB as 490.2227 for the molecule.

The FAB spectrum showed: 491 (M+H) 473 (M+H−$H_2O$), 413 (473−$CH_3COOH$).

<u>¹H NMR data:</u>

| PPM | Form | J(Hertz) |
|---|---|---|
| 0.91 | s | — |
| 1.20 | s | — |
| 2.09 | s | — |
| 3.91 | d | 4.1 |
| 4.09 | d of d | 7.0, 6.9 |
| 4.23 | d | 1.4 |
| 4.38 | d of d | 4.1, 14.9 |
| 5.08 | d of t | 11.3, 3.2, 3.2 |
| 6.28 | d | 1.0 |
| 7.39 | d | 1.8 |
| 7.75 | d of d | 9.8, 2.5 |

The ¹H NMR spectrum showed good agreement with the literature values.

ANTIVIRAL ACTIVITIES OF THE COMPOSITIONS OF THE INVENTION

The following assay methods were utilized to demonstrate the in vitro antiviral effectiveness of compounds 1–4 as reported in Table 1.

Antiviral Disc Assay for HSV-1 and VSV

A. Maintenance of Cell Cultures
 1. Virus: Both herpes simplex type 1 (HSV-1) and vesicular stomatitis virus (VSV) replicate in the CV-1 cell line. CV-1 is a fibroblast-like cell culture derived from primary African green monkey cells.
 2. Growth of CV-1 Cells
  a. Seed 150 cm² tissue culture flasks each with $10 \times 10^6$ CV-1 cells in 40 mL of growth medium EMEM (Eagle's minimal essential medium and Earle's balanced salt solution) with 10% FBS (fetal bovine serum).
  Seven days after seeding the flasks, cell numbers should be approximately $40-50 \times 10^6$ cells.
 3. Trypsinization
  a. Aseptically remove the medium.
  b. Rinse cell sheet with 10 mL of Ca++ and Mg++ free Dulbecco's phosphate buffered saline or Pucks G saline at least twice.
  c. Add 1.5 to 2.0 mL of trypsin-EDTA mixture.
  d. Incubate flask at room temperature or at 37° C. with occasional rocking until the cells detach from the flask (about 15–30 min).
  e. Add 10 mL EMEM growth medium and break up cell clumps with pipetting.
  f. Count cells.
B. Preparation of plates for viral assays
 1. Cell Concentration
  a. Dilute the cells with EMEM to $4 \times 10^5$ cells/mL. Seed 24-well trays with 0.5 mL per well. Cell concentration per well is $2 \times 10^5$ cells.
  c. Incubate at 37° C. with 5% $CO_2$.
  d. The wells can be used over the next several days beginning the day after seeding (preferably 2, 3, or 4).
C. Assay of HSV-1 and VSV in CV-1 cells
 1. Infection of CV-1 cells in plates with virus.

a. Remove medium from wells.
b. Infect well with at least 25 and no more than 80 plaque-forming units (PFU) of virus.
c. Incubate infected cells at 37° C. for 1.5 hours.
d. Pour off supernatant at end of incubation period.
e. Add 0.5 mL of methylcellulose overlay maintenance medium without phenol red made with 1% 4000 centipoise methylcellulose(MCO).

2. Compound Evaluation
a. Wet filter paper discs (6-mm diameter) with approximately 0.02 mL of test compound and allow solvent to evaporate for 20 to 30 minutes at room temperature.
b. Place discs in the well containing CV-1 cells, virus, and MCO, Incubate tissue culture plates for 48 hours at 37° C. and after 48 hours, place 0.5 mL NRMCO on each well. (NRMCO is a maintenance overlay medium without phenol red containing 0.1 mg neutral red dye per mL and 2% 15 centipoise methylcellulose.)
c. Incubate plates at 37° C. and read the following day. Antiviral activity should be observed from two parameters. One is actual reduction in the number of plaques and two is the diminution in plaque diameter.

3. Scoring Activity
a. Antiviral activity:
+++ =complete inhibition of plaque formation
++ =partial inhibition
+ =partial inhibition
+/− =marginal inhibition
− =no protection
b. Cytotoxicity:
0=no visual or microscopic cytotoxicity
16=complete cell destruction
8, 10, 12, 14=partial cytotoxicity

TABLE 1

| Antiviral results | | | VSV | | HSV-1 | |
|---|---|---|---|---|---|---|
| Composition | Dose per/well | | cyt | av | cyt | av |
| 1 | 200 | μg | 0 | ++ | 0 | +++ |
|   | 100 |    | 0 | ++ | 0 | +++ |
|   | 50  |    | 0 | ++ | 0 | +++ |
|   | 25  |    | 0 | ++ | 0 | +++ |
|   | 12.5|    | 0 | ++ | 0 | +++ |
|   | 6.25|    | 0 | ++ | 0 | +++ |
|   | 25  |    | 0 | ++ | 0 | +++ |
|   | 12.5|    | 0 | ++ | 0 | +++ |
|   | 6.25|    | 0 | ++ | 0 | +++ |
|   | 3.13|    | 0 | ++ | 0 | +++ |
|   | 1.56|    | 0 | ++ | 0 | +++ |
|   | 0.78|    | 0 | ++ | 0 | +++ |
|   | 300 | ng | 0 | +  | 0 | ++ |
|   | 100 |    | 0 | +  | 0 | +  |
|   | 30  |    | 0 | +  | 0 | +  |
|   | 20  |    | 0 | +  | 0 | +  |
|   | 10  |    | 0 | ±  | 0 | −  |
|   | 3   |    | 0 | −  | 0 | −  |
| 2 | 300 | ng | 0 | ++ | 0 | ++ |
|   | 100 |    | 0 | +  | 0 | +  |
|   | 30  |    | 0 | +  | 0 | +  |
|   | 10  |    | 0 | −  | 0 | −  |
|   | 3   |    | 0 | −  | 0 | −  |
| 3 | 300 | ng | 0 | +  | 0 | ++ |
|   | 100 |    | 0 | +  | 0 | ++ |
|   | 30  |    | 0 | +  | 0 | +  |
|   | 10  |    | 0 | ±  | 0 | +  |
|   | 3   |    | 0 | −  | 0 | −  |
| 4 | 300 | ng | 0 | +  | 0 | ++ |
|   | 100 |    | 0 | +  | 0 | ++ |
|   | 30  |    | 0 | −  | 0 | +  |
|   | 10  |    | 0 | −  | 0 | ++ |

TABLE 1-continued

| Antiviral results | | VSV | | HSV-1 | |
|---|---|---|---|---|---|
| Composition | Dose per/well | cyt | av | cyt | av |
|   | 3 | 0 | − | 0 | + |

Controls: Ribavirin (VSV) 100 μg +++, 10 μg ++, 1 μg −; ARA A (HSV-1) 100 μg +++, 10 μg +, 1 μg −; Acyclovir (HSV-1) 100 μg +++, 10 μg +++, 1 μg ++, 0.1 μg ++

The results in Table 1 indicate that the compounds of the invention as represented by compounds 1–4 are effective for controlling VSV, and HSV-1 in vitro, in concentrations as low as 3.0 ng/well. The results are indicative of the utility of the compounds of the invention to control viruses in vitro and in vivo in hosts both animal and plant, as well as the diseases caused by viruses.

Application of the compositions of the present invention can be accomplished by any suitable therapeutic method and technique as is presently or prospectively known to those skilled in the art. Therapeutic methods of the invention comprise the administration of antiviral effective amounts of one or more of the compounds of the invention or their pharmaceutically acceptable salts, as an active ingredient, together with desired pharmaceutically acceptable diluents, adjuvants and carriers, to an animal suffering from a virus induced disease state.

The pharmaceutically acceptable salts of the compounds of the present invention may be prepared by conventional reactions with equivalent amounts of organic or inorganic solutions. Pharmaceutically acceptable salts may include but are not limited to salts of hydrochloric, hydrobromic, sulfuric, benzenesulphonic, acetic, fumaric, oxalic, malic and citric acids, and hydroxides of potassium and sodium.

The compositions may be administered parenterally in combination with conventional injectable liquid carriers such as sterile pyrogen-free water, sterile peroxide-free ethyl oleate, dehydrated alcohol or propylene glycol. Conventional pharamceutical adjuvants for injection solutions such as stabilizing agents, solubilizing agents and buffers, for example, ethanol, complex form agents such as ethylene diamine tetraacetic acid, tartrate and citrate buffers and high-molecular weight polymers such as polyethylene oxide for viscosity regulation may be added. Such compositions may be injected intramuscularly, intraperitoneally, or intravenously.

The compositions may also be formulated into orally adminstrable compositions containing one or more physiologically compatible carriers or excipients, and may be solid or liquid in form. These compositions may, if desired, contain conventional ingredients such as binding agents, for example, syrups, acacia, gelatin, sorbitol, tragacanth, or polyvinylpyrolidone; fillers, for example, lactose, mannitol, starch, calcium, phosphate, sorbitol or methylcellulose; lubricants, for example, magnesium stearate, high-molecular weight polymers such as polyethylene glycols, high-molecular weight fatty acids such as stearic acid or silica; disintegrants, for example, starch; acceptable wetting agents as, for example, sodium lauryl sulfate. These compositions may take any convenient form, for example, tablets, capsules, emulsions, or dry products suitable for reconstitution with water or other liquid medium before use. The liquid oral forms of administration may, of course, contain flavors; sweeteners; preservatives, for example, methyl or propyl p-hydroxybenzoates; suspending agents, for example, sorbitol; emulsifying agents, for example, lecithin or sorbitan monooleate; or thickening agents. Non-aqueous compositions may also be formulated which comprise edible oils as, for example, fish-liver or vegetable oils. These liquid compositions may conveniently be encapsulated in, for example, gelatin capsules in a unit dosage amount.

The pharmaceutical compositions according to the present invention may also be administered, if appropriate, topically as an aerosol or, formulated with conventional bases, as a cream or ointment.

The antiviral compositions of the invention may also have agricultural applications and can be applied to plants by suitable means, e.g., spraying.

Unit dosage forms of compounds administered according to the methods of the invention may be formulated by those skilled in the art to provide effective daily dosages that vary in accordance with body weight of the animal to be treated. The scope of the present invention is not limited by the description, examples, and suggested uses herein and modifications can be made without departing from the spirit of the invention. For example, it may be noted that other derivatives of the compounds of examples 1-5 such as halogenated derivatives may possess antiviral activity analogous to those preferred embodiments described above. Further, the compositions described herein may have other useful applications such as, for example, analgesic, antitumor or antibacterial applications. It is therefore intended that the present invention cover the modifications and variations of this invention provided that they come within the scope of the appended claims and their equivalents.

What is claimed is:

1. A method for inhibiting plaque-forming viruses selected from the group consisting of RNA viruses and DNA viruses comprising contacting said virus with an amount effective to inhibit the activity of the virus of a compound according to the formula:

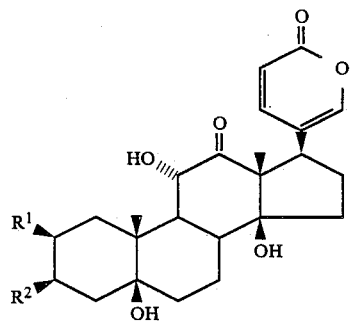

wherein $R^1$ and $R^2$ are the same or different and are each a hydroxyl or lower acyloxy group.

2. A method according to claim 1 for inhibiting plaque-forming viruses selected from the group consisting of RNA viruses and DNA viruses comprising contacting said virus with an amount effective to inhibit the activity of the virus of one or more of the following compounds:

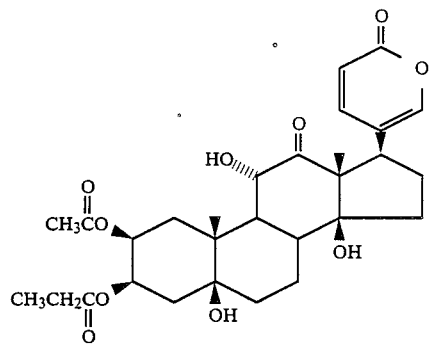

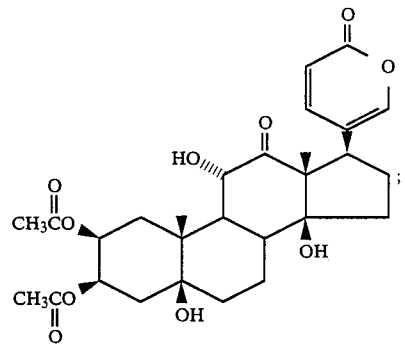

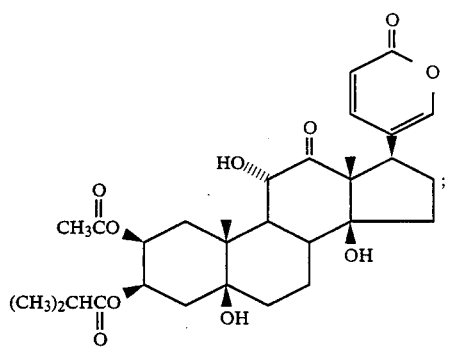

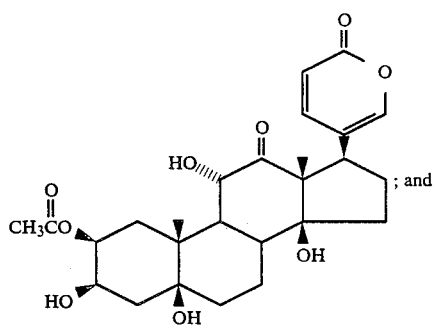

-continued

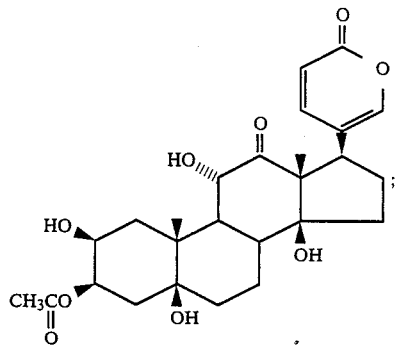

V

3. A method according to claim 2 wherein the effective amount is between about 30 to 300 nanograms against 25 to 80 plaque forming units of virus.

4. A method according to claim 2 wherein the DNA viruses are selected from the group consisting of herpes viruses, adenoviruses, coxsackie viruses and papovaviruses.

5. A method according to claim 4 wherein the RNA virus is herpes simplex-I.

6. A method according to claim 2 wherein the active agent is administered to an infected host by means of a parenteral, oral, aerosol or spray formulation.

7. A method according to claim 6 wherein the infected host is a mammalian host.

8. A method according to claim 1 wherein the effective amount is 3 to 30 nanograms against 25 to 80 plaque forming units of virus.

9. A method according to claim 1 wherein the RNA viruses are selected from the group consisting of vesicular stomatitis, arenaviruses, corona viruses, rhineoviruses, reoviruses, polioviruses, influenza viruses.

10. A method according to claim 9 wherein the RNA virus is vesicular stomatitis.

11. A method according to claim 1 wherein the active agent is administered to an infected host by means of a parenteral, oral, aerosol or spray formulation.

12. A method according to claim 11 wherein the infected host is a mammalian host.

13. A process for isolating a compound from *Photinus pyralis* selected from the group consisting of:

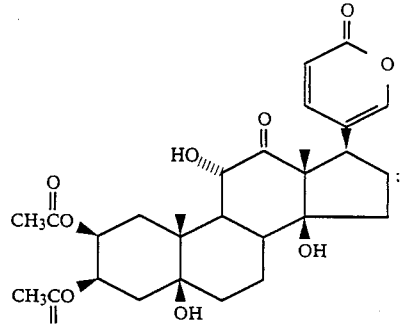

III

-continued

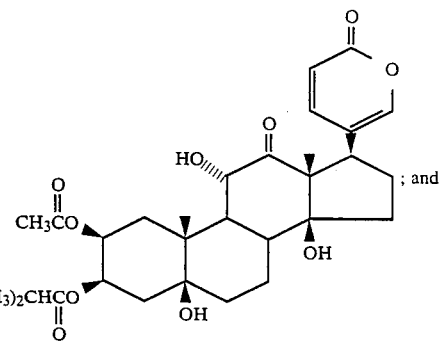

II

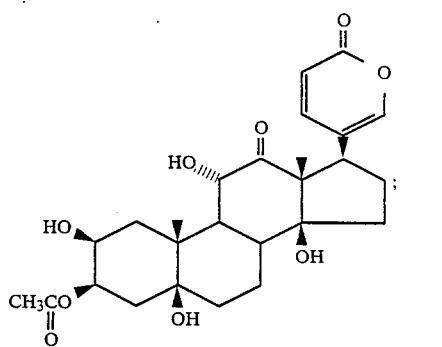

IV
; and

V comprising the following steps:
A. thoroughly grinding a sufficient number of *Photinus pyralis* to provide at least about 5 g dry weight with a first organic solvent selected from the group consisting of benzene, hexane, toluene, chloroform, methylene chloride, ethylacetate, butyl acetate, methanol, ethanol, butanol, acetone, acetonitrile and mixtures thereof;
B. filtering the ground mixture to remove the solids;
C. evaporating the first organic solvent to obtain a residue;
D. partially redissolving the residue in a second organic solvent selected from the group consisting of benzene, hexane, toluene, chloroform, methylene chloride, ethylacetate butyl acetate, methanol, ethanol, butanol, acetone, acetonitrile and mixtures thereof;
E. passing the filtrate by gravity chromatography through a silica gel packed minicolumn to obtain an eluate;
F. separating the compound by injecting the eluate onto a HLPC system using an Alltech 6233 10 um silica column to collect fractions 1 to 4 containing the following compounds:
fraction 1—compound II, pure 12-oxo-2,3,-di-O-acetyl-2β,5β,11α-trihydroxybufalin;

2—compound IV, curde 12-oxo-2-O-acetyl-3-O-isobutyryl-2β,5β,11α-trihydroxybufalin;

3—compound III, crude 12-oxo-2-O-acetyl-3-O-propionyl-2β,5β,11α-trihydroxybufalin;

4—compound V crude 12-oxo-3-O-acetyl-2β,5β,11α-trihydroxybufalin.

14. A process according to claim 13 further comprising:

G. further purifying fractions 2 to 3 by
  (i) passing fraction 2 through the HPLC by using 30 to 35% hexane in ethylacetate as a solvent;
  (ii) passing fraction 3 through the HPLC by using 20% hexane in ethylacetate as a solvent; and
  (iii) passing fraction 4 through an HPLC system using a degraded silica column with about one third the elution volume of the Alltech 6233 column using ethylacetate as a solvent.

15. A process according to claim 13 wherein the first and second organic solvents are ethylacetate.

16. A process for isolating compound VI, 12-oxo-2-O-acetyl-2β,5β,11α-trihydroxybufalin, from *Photinus pyralis* by:

A. adding methanol to a sufficient number of *Photinus pyralis* to provide at least 5 g dry weight in a sufficient volume to cover the weight of dead insects;

B. preserving the mixture for at least about six months;

C. filtering the mixture to remove the dead insects and adjusting the volume to 800 ml;

D. adding 400 ml of 1N sodium chloride;

E. extracting the mixture with methylene chloride;

F. heating gently the methylene chloride extract to remove the methylene chloride to obtain a residue;

G. dissolving the residue in about 200 ml 3:1 methanol:toluene and partitioning the mixture against 100 ml of 1N sodium chloride;

H. removing the lower toluene layer;

I. evaporating the toluene to obtain a second residue;

J. dissolving the second residue in methanol;

K. purifying the methonal mixture by HPLC using a Alltech/Applied Science 6231 25 cm, 10 mm i.d. 10 um $C_{18}$ column with methanol as the solvent, at a pump rate of 6.0 ml per minute to collect a fraction with a retention time of about four minutes;

L. removing the methanol by evaporation and redissolving the mixture in ethylacetate; and M. injecting the ethylacetate mixture into an HPLC with an Alltech 6233 column and collecting fraction 7.

* * * * *

UNITED STATES PATENT AND TRADEMARK OFFICE
CERTIFICATE OF CORRECTION

PATENT NO. : 4,847,246
DATED : July 11, 1989
INVENTOR(S) : Wilson et al.

It is certified that error appears in the above-indentified patent and that said Letters Patent is hereby corrected as shown below:

Column 1, line 4, insert the following information:

--This invention was made with Government support under Grant No. AI04769 and GM 27029 awarded by the National Institutes of Health. The Government has certain rights in the invention."

Signed and Sealed this

Second Day of May, 1995

Attest:

BRUCE LEHMAN

Attesting Officer

Commissioner of Patents and Trademarks